(12) United States Patent
Yeh et al.

(10) Patent No.: US 6,417,376 B1
(45) Date of Patent: Jul. 9, 2002

(54) SELECTIVE OXIDATION PROCESS AND CATALYST THEREFOR

(75) Inventors: Chuen Y. Yeh, Edison; Lawrence L. Murrell, South Plainfield; Pal Rylandshom, Hoboken; Robert E. Trubac, Ridgewood; Rudolf A. Overbeek, Chatham Township; Chiung Y. Huang, Glen Ridge; Cemal Ercan, Bloomfield; Nelleke Vander Puil, Hoboken; Herbert E. Barner, Kinnelon, all of NJ (US)

(73) Assignee: ABB Lummus Global Inc., Bloomfield, NJ (US)

(*) Notice: Subject to any disclaimer, the term of this patent is extended or adjusted under 35 U.S.C. 154(b) by 0 days.

(21) Appl. No.: 09/407,436
(22) Filed: Sep. 29, 1999

Related U.S. Application Data
(60) Provisional application No. 60/103,717, filed on Oct. 9, 1998.

(51) Int. Cl.$^7$ .................. B01J 27/198; B01J 35/06; C07D 307/89; C07D 301/10; C07D 45/32
(52) U.S. Cl. .............. 549/248; 549/534; 549/259; 562/532; 568/472; 568/475; 568/479; 502/209; 502/305; 502/348; 502/350
(58) Field of Search ................ 549/248, 534; 568/475, 479; 502/209, 305, 348, 350; 562/532

(56) References Cited

U.S. PATENT DOCUMENTS

| | | | |
|---|---|---|---|
| 3,713,281 A | 1/1973 | Asker et al. .................. 55/387 |
| 4,686,202 A | 8/1987 | Broecker ..................... 502/300 |
| 5,080,963 A | 1/1992 | Tatarchuk et al. .......... 428/225 |
| 5,096,663 A | 3/1992 | Tatarchuk ..................... 419/11 |
| 5,102,745 A | * 4/1992 | Tatarchuck et al. ......... 428/605 |
| 5,304,330 A | 4/1994 | Tatarchuk et al. ............. 264/61 |

FOREIGN PATENT DOCUMENTS

| | | |
|---|---|---|
| DE | 3213413 | 10/1983 |
| EP | 61304 | 9/1982 |
| EP | 218124 | 4/1987 |
| EP | 423692 | 4/1991 |
| JP | 58-153538 | 9/1983 |
| WO | WO 99/07467 | 2/1999 |

* cited by examiner

Primary Examiner—Bernard Dentz
(74) Attorney, Agent, or Firm—Elliot M. Olstein; Raymond J. Lillie

(57) ABSTRACT

A process for selectively oxidizing an organic molecule by reacting said organic molecule and oxygen in the presence of a selective oxidation catalyst supported on a mesh-like structure.

15 Claims, No Drawings

SELECTIVE OXIDATION PROCESS AND CATALYST THEREFOR

This application claims the priority of United States Provisional Application Serial No. 60/103,717 filed on Oct. 9, 1998.

This invention relates to chemical products that are made via selective oxidation. More particularly, this invention relates to selective oxidation in the presence of a catalyst which is supported on a mesh-like structure.

In the petrochemical industry there are produced products that are made via selective oxidation. By selective oxidation is meant that the feed component is reacted with molecular oxygen or molecular oxygen containing streams such as air with the reaction being stopped before complete oxidation to carbon dioxide and water.

For example, phthalic anhydride is produced by a selective oxidation process. Most plants for producing phthalic anhydride employ a multi-tubular reactor filled with inert (Raschig) rings or beads coated with an active catalyst. The reaction is highly exothermic and often excessive oxidation of the product, phthalic anhydride, occurs due to poor temperature control or heat removal. Conversion of o-xylene is virtually complete, but selectivity to phthalic anhydride is well below 100%. The best commercial processes are known to have a yield of about 80%.

Ethylene oxide also is commercially produced by a selective oxidation process involving the epoxidation of ethylene over a catalyst which catalyzes the production of ethylene oxide. In general, the catalyst which is employed for such production is a silver containing catalyst, which is supported on a suitable support.

The production of ethylene oxide is an exothermic reaction and. in general, in order to remove the heat of reaction ethylene oxide is produced in a tubular reactor in which the gaseous ethylene, and a gas containing oxygen are reacted in the gaseous phase over a bed of supported catalyst in a plurality of tubes, with the exothermic heat of reaction being removed by use of a circulating coolant which surrounds the tubes.

The yield of ethylene oxide is dependent upon both the rate of conversion of ethylene to ethylene oxide, and the selectivity of such conversion. In general, higher temperatures increase conversion and decrease selectivity, whereby conversion is balanced against selectivity in order to obtain an appropriate yield. In general, there have been attempts to improve the yield of ethylene oxide by employing a variety of promoters in combination with the silver containing catalyst which is commercially employed for such ethylene oxide production.

The yield of acrylic acid is dependant upon the conversion and selectivities in the oxidation of propylene or propane to acrolein and the further oxidation of acrolein to acrylic acid. In general, higher temperatures increase conversion and decrease selectivity, whereby conversion is balanced against selectivity in order of obtain an appropriate yield. Attempts have been made to increase selectivity by modifications to the mixed oxide catalyst normally used.

As a result, there is a need for improvements in processes for the selective oxidation of organic compounds by the use of molecular oxygen.

In accordance with one aspect of the present invention there is provided a selective oxidation process wherein an organic compound is reacted with molecular oxygen in the presence of a suitable oxidation catalyst, with such catalyst being supported on a particulate support wherein such supported catalyst is supported on a non-particulate catalyst support structure that is a mesh-like material. The term "supported on the mesh" includes coating the supported catalyst on the mesh as well as entrapping the supported catalyst in the interstices of the mesh.

The supported catalyst supported on the mesh is used as a fixed bed. The reaction is preferably in the gas phase.

More particularly, the mesh like material is comprised of fibers or wires, such as a wire or fiber mesh, a metal felt or gauze, metal fiber filter or the like. The mesh like structure may be comprised of a single layer, or may include more than one layer of wires (e.g. a knitted wire structure or a woven wire structure), and is preferably comprised of a plurality of layers of wires or fibers to form a three-dimensional network of materials. In a preferred embodiment, the support structure is comprised of a plurality of layers of fibers that are randomly oriented in the layers. One or more metals may be used in producing a metal mesh. Alternatively the mesh fibers may be formed from or include materials other than metals alone or in combination with metals; e.g. carbon, metal carbides, metal oxides, or a ceramics.

In a preferred embodiment wherein the mesh-like structure is comprised of a plurality of layers of fibers to form the three-dimensional network of materials, the thickness of such support is at least five microns, and generally does not exceed ten millimeters. In accordance with a preferred embodiment, the thickness of the network is at least 50 microns and more preferably at least 100 microns and generally does not exceed 2 millimeters.

In general, the thickness or diameter of the fibers which form the plurality of layers of fibers is less than about 500 microns, preferably less than about 150 microns and more preferably less than about 30 microns. In a preferred embodiment, the thickness or diameter of the fibers is from about 8 to about 25 microns.

The three-dimensional mesh-like structure may be produced as described in U.S. Pat. Nos. 5,304,330; 5,080,962; 5,102,745; or 5,096,663. It is to be understood, however, that such mesh-like structure may be formed by procedures other than as described in the aforementioned patents.

The mesh-like structure that is employed in the present invention (without supported catalyst on the mesh) has a void volume which is at least 45%, and is preferably at least 55% and is more preferably at least 65% and still more preferably is at least about 85% (for example, at least 90%). In general, the void volume does not exceed about 98%. The term "void volume" as used herein is determined by dividing the volume of the structure which is open by the total volume of the structure (openings and mesh material) and multiplying by 100. In general, the average void opening is at least 10 microns and preferably at least 20 microns.

The catalyst support on which the catalyst is supported, with such supported catalyst then being supported on a mesh like structure, is a support that is in particulate form. The term particulate as used herein includes and encompasses spherical particles, elongated particles, fibers, etc. In general, the average particle size of the particulate on which the selective oxidation catalyst is supported does not exceed 200 microns and is typically no greater than 50 microns with the average particle size in the majority of cases not exceeding 20 microns. In general, the average particle size of such particulates is at least 0.002 micron and more generally at least 0.5 microns. When the catalyst supported on the particulate support is coated on the mesh, the average particle size of the catalyst support generally does not exceed 10 microns and, when entrapped in the mesh, generally does not exceed 150 microns.

In accordance with a preferred aspect of the present invention, the selective oxidation is effected in a fixed bed and the particulate support has an average particle size as hereinabove described, which size is significantly smaller than those used in prior art fixed bed processes.

In an embodiment of the invention, the mesh-like structure, that functions as a support for the oxidation catalyst supported on a particulate support is in the form of a shaped structured packing. This packing can be configured to provide for turbulence of the gas phase flowing over the catalyst in the selective oxidation reactor. The mesh-like catalyst support structure may be provided with suitable corrugations in order to provide for increased turbulence. Alternatively, the mesh-like structure may include tabs or vortex generators to provide for turbulence. The presence of turbulence generators permits mixing in the radial (and longitudinal) direction and permits improved heat transfer at the wall compared to the processes know in the art. This can be effected by adding turbulence generators to the structure that contact the wall. The improved heat transfer characteristics at the wall lead to an overall lower temperature and consequently higher selectivity. The structural packing can also be in the form of a module such as a roll of one or more sheets that is placed into the tubes of a reactor such that the channels in the module follow the longitudinal direction of the tube. The roll can comprise sheets that are flat, corrugated or wavy or a combination thereof and the sheets can contain fins or holes to promote mixing. The sheets can also be shaped into corrugated strips that are separated from each other by a flat sheet that exactly fit the size of the tube and are held together by welds, wires, a cylindrical flat sheet or combinations thereof.

It is to be understood that the mesh-like support that supports the supported catalyst may be employed in a form other than as a structured sheet. For example, the mesh-like support may be formed as rings, particles, ribbons, etc. and employed in the reactor as a packed bed. In one embodiment the particle dimensions are smaller than those of packed bed particles that are known in the prior art.

The supported selective oxidation catalyst which is supported on the mesh like structure may be present on the mesh like support as a coating on the wires or fibers that form the mesh-like structure and/or may be present and retained in the interstices of the mesh-like structure.

In one embodiment, wherein the catalyst supported on a particulate support is present as a coating on the mesh like catalyst structure, the mesh like catalyst structure may be initially coated with the particulate support, followed by addition of the selective oxidation catalyst to the particulate support present as a coating on the mesh-like structure. Alternatively, the catalyst supported on a particulate support may be coated onto the mesh. The particulate support with or without catalyst may be coated on the mesh-like structure by a variety of techniques, e.g., dipping or spraying.

The supported catalyst particles may be applied to the mesh-like structure by contacting the mesh-like structure with a liquid coating composition (preferably in the form of a coating bath) that includes the particles dispersed in a liquid under conditions such that the coating composition enters or wicks into the mesh-like structure and forms a porous coating on both the interior and exterior portions of the mesh-like structure.

Alternatively, the mesh-like structure is coated with a particulate support containing active catalyst or the mesh-like structure may be coated with particles of a catalyst precursor.

In a preferred embodiment, the liquid coating composition has a kinematic viscosity of no greater than 175 centistokes and a surface tension of no greater than 300 dynes/cm.

In one embodiment, the supported catalyst or catalyst support is coated onto the mesh by dip-coating. In a preferred embodiment, the three-dimensional mesh-like material is oxidized before coating; e.g., heating in air at a temperature of from 300° C. up to 700° C. In some cases, if the mesh-like material is contaminated with organic material, the mesh-like material is cleaned prior to oxidation; for example, by washing with an organic solvent such as acetone.

The coating bath is preferably a mixed solvent system of organic solvents and water in which the particles are dispersed. The polarity of the solvent system is preferably lower than that of water in order to prevent high solubility of the catalyst and to obtain a good quality slurry for coating. The solvent system may be a mixture of water, amides, esters, and alcohols. The kinematic viscosity of the coating bath is preferably less than 175 centistokes and the surface tension thereof is preferably less than 300 dynes/cm.

In a preferred embodiment of the invention, the mesh-like structure that is coated includes metal wires or fibers and the metal wires or fibers that are coated are selected or treated in a manner such that the surface tension thereof is higher than 50 dynes/cm, as determined by the method described in "*Advances in Chemistry*, 43, *Contact Angle, Wettability and Adhesion, American Chemical Society*, 1964."

In coating a mesh-like structure that includes metal fibers, the liquid coating composition preferably has a surface tension from about 50 to 300 dynes/cm, and more preferably from about 50 to 150 dynes/cm, as measured by the capillary tube method, as described in T. C. Patton, "Paint Flow and Pigment Dispersion", $2^{nd}$ Ed., Wiley-Interscience, 1979, p. 223. At the same time, the liquid coating composition has a kinematic viscosity of no greater than 175 centistokes, as measured by a capillary viscometer and described in P. C. Hiemenz, "Principles of colloid and Surface Chemistry", $2^{nd}$ Ed., Marcel Dekker Inc., 1986, p. 182.

In such an embodiment, the surface tension of the metal being coated is coordinated with the viscosity and surface tension of the liquid coating composition such that the liquid coating composition is drawn into the interior of the structure to produce a particulate coating on the mesh-like structure. The metal to be coated preferably has a surface tension which is greater than 50 dynes/cm and preferably is higher than the surface tension of the liquid coating composition to obtain spontaneous wetting and penetration of the liquid into the interior of the mesh.

In the case where the metal of the structure that is to be coated does not have the desired surface tension, the structure may be heat-treated to produce the desired surface tension.

The liquid coating composition can be prepared without any binders or adhesives for causing adherence of the particulate coating to the structure.

The surface of the structure to be coated may also be chemically or physically modified to increase the attraction between the surface and the particles that form the coating; eg., heat treatment or chemical modification of the surface.

The solids content of the coating bath generally is from about 2% to about 50%, preferably from about 5% to about 30%.

The bath may also contain additives such as surfactants, dispersants etc. In general, the weight ratio of additives to particles in the coating bath is from 0.0001 to 0.4 and more preferably from 0.001 to 0.1.

The mesh-like material preferably is coated by dipping the mesh-like material into a coating bath one or more times while drying or calcining in between dippings. The temperature of the bath is preferably at room temperature, but has to be sufficiently below the boiling point of the liquid in the bath.

After coating, the mesh-like material that includes a porous coating comprised of a plurality of particles is dried, preferably with the material in a vertical position. The drying is preferably accomplished by contact with a flowing gas (such as air) at a temperature of from 20° C. to 150° C. more preferably from 100° C. to 150° C. After drying, the coated mesh-like material is preferably calcined, for example, at a temperature of from 250° C. to 800° C., preferably 300° C. to 500° C., most preferably at about 400° C. In a preferred embodiment, the temperature and air flow are coordinated in order to produce a drying rate that does not affect adversely the catalyst coating, e.g., cracking, blocking of pores, etc. In many cases, a slower rate of drying is preferred.

The thickness of the formed coating may vary. In general, the thickness is at least 1 micron and in general no greater than 100 microns. Typically, the coating thickness does not exceed 50 microns and more typically does not exceed 30 microns.

The interior portion of the mesh material that is coated has a porosity which is sufficient to allow the particles which comprise the coating to penetrate or migrate into the three dimensional network. Thus, the pore size of the three dimensional material and the particle size of the particles comprising the coating, in effect, determine the amount and uniformity of the coating that can be deposited in the interior of the network of material and/or the coating thickness in the network. The larger the pore sizes the greater the thickness of the coating which can be uniformly coated in accordance with the invention.

In the case where the particles are in the form of a catalyst precursor, the product, after the deposit of the particles, is treated to convert the catalyst precursor to an active catalyst. In the case where the particles which are deposited in the three dimensional network of material is a catalyst support, active catalyst or catalyst precursor may then be applied to such support, e.g., by spraying, dipping, or impregnation.

In using a coating bath, the coating bath in some cases may include additives. These additives change the physical characteristics of the coating bath, in particular the viscosity and surface tension such that during dipping penetration of the mesh takes place and a coating can be obtained with a homogeneous distribution on the interior and exterior of the mesh. Sols not only change the physical properties of the coating bath, but also act as binders. After the deposition, the article is dried and calcined.

As representative stabilizing agents there may be mentioned: a polymer like polyacrylic acid, acrylamines, organic quaternary ammonium compounds, or other special mixes which are selected based on the particles. Alternatively an organic solvent can be used for the same purpose. Examples of such solvents are alcohols or liquid paraffins. Control of the pH of the slurry, for example, by addition of $HNO_3$ is another method of changing the viscosity and surface tension of the coating slurry.

The particulate support with or without catalyst may be coated onto the mesh like catalyst support by an electrophoretic coating procedure, as described in U.S. application Ser. No. 09/156,023, filed on Sep. 17, 1998 now U.S. Pat. No. 6,207,732. In such a procedure, a wire mesh like structure is employed as one of the electrodes, and the particulate support of the requisite particle size, with or without catalyst, (which preferably also includes the support in the form of a sol to promote the adherence of larger particles to the wire mesh) is suspended in a coating bath. A potential is applied across the electrodes, one of which is the mesh like structure formed from a plurality of layers of fibers, and the mesh like structure is electrophoretically coated with the support with or without catalyst. If the support does not include a catalyst, the phthalic anhydride catalyst is then added to the catalyst structure by dipping the structure (which contains the support as a coating) into an appropriate solution that contains the catalyst and preferably one or more promoters.

As hereinabove indicated, the supported selective oxidation catalyst may be supported on the mesh material by entrapping or retaining the particulate support in the interstices of the mesh. For example, in producing a mesh like structure comprised of a plurality of layers of randomly oriented fibers, the particulate support may be included in the mix that is used for producing the mesh-like structure whereby the mesh-like structure is produced with the particulate support retained in the interstices of the mesh. For example, such mesh like structure may be produced as described in the aforementioned patents, and with an appropriate particulate support being added to the mesh that contains the fibers and a binder, such as cellulose. The produced mesh structure includes the support particles retained in the mesh structure. The particulate support retained in the mesh structure is then impregnated with selective oxidation catalyst by procedures known in the art.

These and other embodiments should be apparent to those skilled in the art from the teachings herein.

Although in a preferred embodiment, essentially the entire thickness of the material is coated with the catalyst, it is within the spirit and scope of the invention to coat less than the entire thickness with such particles. It also is possible within the spirit and scope of the present invention to have various coating thicknesses within the three-dimensional structure.

The catalyst structure of the present invention may be employed in a selective oxidation process using oxidation procedures generally known in the art, however, there is an improved yield. The improved yield may be obtained by increasing rates of conversion in that increased selectivity can be obtained and/or from the increased selectivity at previously used rates of conversion.

In accordance with another aspect of the present invention, the oxidation catalyst (catalyst supported on a particulate support) is supported on the mesh-like structure in an amount of at least 5%, and preferably at least 10%, with the amount of supported catalyst generally not exceeding 80% and more generally not exceeding 50%, all by weight, based on mesh and supported catalyst. In one embodiment where the void volume of the mesh-like structure prior to adding supported catalyst is about 90%, the weight percent of supported catalyst is from about 5% to about 40% and when the void volume is about 95% the weight percent of supported catalyst is from about 5% to about 80%. In a preferred embodiment, the mesh-like structure that includes supported catalyst is employed in an amount to provide a void volume in the reaction zone of at least 60% and preferably at least 70%. In general, in such a preferred embodiment, the void volume does not exceed about 95%.

In an embodiment of the invention, the selective oxidation is effected in a tubular reactor, with the catalyst structure being inserted into the tubes in which the organic compound and oxygen are reacted. In such an embodiment of the invention, the mesh-like structure, which functions as a support for the catalyst is shaped to provide for turbulence of the gas phase flowing over the catalyst and for break-up of the laminar layer at the wall of the reactor tube. The mesh-like catalyst support structure may be provided with suitable corrugations in order to provide for turbulence in the tube and for an increased number of contact points at the reactor wall compared to the packed beds know in the prior art.

The present invention is applicable to a wide variety of processes for catalytic selective oxidation of an organic compound by the use of molecular oxygen. In most cases, the organic compound is a hydrocarbon; for example, an aromatic hydrocarbon or a saturated or unsaturated aliphatic hydrocarbon. As representative examples, there may be mentioned processes for selectively oxidizing naphthalene and/or o-xylene to phthalic anhydride; benzene, butane and/or butene to maleic anhydride; an aliphatic hydrocarbon to the corresponding epoxy compound, such as an alkene to an alkylene oxide; a primary alcohol to an aldehyde (for example, oxidation of methyl alcohol to form formaldehyde); an alkene or alkane to an aldehyde (for example, propene and/or propane to acrolein); an aldehyde to a carboxylic acid (for example, acrolein to acrylic acid), etc.

For example, the partial oxidation of propylene is normally carried out in a two-stage system. The reaction feed gas, a mixture of propylene, steam and air preheated to a heat exchanger is fed to the first reactor in which oxidation of propylene to acrolein ($CH_2=CH-CHO$) takes place in the presence of a catalyst comprised of oxides of multivalent metals (with molebdenum as a main component) at 350–400C (European Pat Appl. 0911311A1).

The reacted gas is then directly introduced to a second reactor, where the main reaction is the oxidation of acrolein to acrylic acid (at 250C–300C). The reaction pressure for both reactors is approximately atmospheric with a contact time of a few seconds (for example, U.S. Pat. No. 4,111,983, U.S. Pat. No. 4,333,858, U.S. Pat. No. 4,410,858, U.S. Pat. No. 4,415,752). The heat of reaction is typically removed by the circulation of a heat transfer medium through the shell side of the reactors, for example, water which is then recovered as steam. In accordance with the present invention, such a process is effected with the selective oxidation catalyst supported on a mesh of the type hereinabove described.

As another representative example of a selective oxidation process, o-xylene is preheated and vaporized into a stream of air. The air contains about 60 to about 100 grams of o-xylene per cubic meter. This concentration of o-xylene is outside the explosive limit. The air/o-xylene mixture then is passed through a multitubular reactor packed with a structured catalyst of the type hereinabove described. The operating pressure is about atrnospheric. A typical 50,000 metric ton plant has about 17,000 tubes, which would be filled with catalyst of the present invention. The reactor is composed of two adjacent in-line reaction zones. Each zone is cooled with a separate salt bath with a catalyst structure of the invention in each zone, however, the catalyst supported thereon can differ in each zone. A eutectic mixture of potassium nitrate and sodium nitrite is used for cooling. The salt temperature in the first zone may be approximately 10° C. higher than that in the second zone. Vanadium and titanium oxides are the major components of the catalyst. A small amount of cesium (or rubidium) oxide is added to the major component of catalyst in the first zone in order to lower the activity of the catalyst. Similarly, a small amount of phosphorus oxide is added to the major component of catalyst in the second zone to increase activity. Gas leaves the reactor at a temperature of about 350° C. to 360° C. The conversion of o-xylene virtually is complete, with the main by-products being carbon dioxide and water. Maleic anhydride, phthalide, and traces of other substances also are formed.

The gas mixture emerging from the reactors is pre-cooled and then fed to a switch condenser system where phthalic anhydride is condensed on the finned tubes as a solid. The switch condensers then are heated by heat transfer oil in an automatic switching cycle. During heating, the deposited phthalic anhydride is melted and collected in a storage tank. Finally, the crude product is purified in two distillation columns.

Heat removal and precise temperature control are crucial for this process. These factors are important not only in order to avoid excessively high temperatures, but also to achieve a better yield. In the use of prior art catalyst structures, large temperature gradients often are present in the radial direction even though the tube diameter is only one inch. This is a result of the high heat of reaction coupled with the poor heat removal capacity from the catalyst bed. The catalyst temperature should be about 340° C. to 350° C., but due to heat transfer limitations and temperature gradients, temperature up to 440° C. at certain hot spots are not uncommon. At these higher temperatures, selectivity toward phthalic anhydride is nearly zero because phthalic anhydride is oxidized to carbon dioxide. By using the catalyst structure of the present invention, there is improved selectivity (improved yield). The following are representative examples of phthalic anhydride catalysts:

Spherical inert supports coated with a thin (0.02 to 2.0 mm thick) layer of catalytically active material comprising vanadium pentoxide and titanium dioxide (ref-DE-A1,442,590). Use has also been made of supported catalysts in which the catalytically active material is doped with phosphorous (U.S. Pat. No. 3,684,741) or with rubidium and/or cesium (U.S. Pat. No. 4,007,136, U.S. Pat. No. 4,096,094, U.S. Pat. No. 5,910,608)

In accordance with the present invention, such selective oxidation is accomplished with the supported catalyst being supported on mesh, as hereinabove described.

In another embodiment, the selective oxidation is a process for selectively epoxidizing an alkene to form an alkylene oxide. An example of this reaction is the epoxidation of ethylene in the gaseous phase to form ethylene oxide. The yield of ethylene oxide is dependant upon both the rate of conversion of ethylene to ethylene oxide, and the selectivity of such conversion. In general , higher temperatures increase conversion and decrease selectivity, whereby conversion is balanced against selectivity in order to obtain an optimum yield. In this embodiment, ethylene is oxidized selectively in the presence of a selective oxidation catalyst supported on a particulate support. The supported catalyst is supported on a mesh-like structure.

In one embodiment, the particulate support that is used for supporting the catalyst for converting an alkene to an alkylene oxide has a surface area of 0.1 to 5 $m^2/g$. In another embodiment, the surface area is greater than the surface area of the catalytic supports previously used in the art. As known in the art, such prior art supports preferably have a surface area from 0.1 to 5 $m^2/g$. Such prior art supports are preferably formed from alpha alumina. In this embodiment, the particular catalyst support is a porous support that has a surface area that is greater than 5 $m^2/g$, and preferably a surface area greater than 25 $m^2/g$. In most cases the surface area does not exceed 300 m$^2$/g. The surface area is measured by the Brunauer, Emmett and Teller (BET) method. The support is a porous support that is heat resistant, and as representative examples of such supports there may be mentioned alumina, silcon carbide, silica, zirconia, titania or a silica/alumina support. The preferred support is a alpha—alumina or transitional alumina, such as gamma-, delta-, or theta- alumina.

As a representative example, alkene and oxygen are reacted in the gaseous phase in the presence of a supported alkylene oxide catalyst supported on a mesh-like support structure in a fixed bed reactor that is preferably a tubular reactor.

Partial pressures of alkene in processes according to the invention may be in the ranges 0.1–30 and preferably 1 to 30 bars. The molar ratio of oxygen to alkene may be in the range 0.05 to 100. The partial pressure of oxygen may be in the range 0.01 and preferably 0.1 to 20 bars and preferably 1–10 bars. The oxygen may be supplied for example in the form of air or preferably as commercial oxygen. A diluent for example helium, nitrogen, argon, carbon dioxide and/or methane may be present in proportions of 10–80% and preferably 40–70% by volume in total. Suitably the diluent comprises methane as aforesaid together with, for example 100 to 20,000 parts per million by volume of ethane, preferably together with small amounts, for example 10 to 10,000 parts per million by volume of $C_3$ to $C_6$ alkanes. It is necessary to operate using gas compositions which are outside the explosive limits.

The temperature is suitably in the range 180 to 320° C., preferably 200 to 300° C. and more preferably in the range 220 to 290° C. Contact times should be sufficient to convert 0.5–70%, for example 2 to 20 and preferably 5–20% of the ethylene and unconverted ethylene is, after separation of the product, suitably recycled, optionally in the presence of unconverted oxygen where appropriate and suitably after partial removal of $CO_2$. Suitably 15 to 50% and preferably 25 to 40% of the oxygen fed is consumed. It is preferred that the $CO_2$ content should be in the range 1% to 10% and more preferably 1.5% to 8% by volume.

The reaction is generally effected in a tubular reactor comprised of a plurality of parallel elongated tubes in a suitable shell, with the shell being provided with a suitable coolant to remove the reaction exotherm. The tubes generally have an inside diameter of from 0.5 to 2.5 inches, with tube lengths being in the order of 15–30 feet.

In a preferred embodiment, the alkylene oxide is produced in a plurality of tubes that contain the supported catalyst supported on a mesh-like structure with the pressure drop through the tubes being less than 2 bar, preferably less than 1.75 bar.

The invention now will be described with respect to the following examples; the scope of the present invention, however, is not intended to be limited thereby.

EXAMPLE 1

A mixed solvent was prepared by mixing 279.0 grams of distilled water and 46.5 grams of formamide. A mixture of 144.5 grams of anatase, 26.5 grams of vanadyl oxalate, 3.9 grams of antimony trioxide, and 0.19 grams of rubidium carbonate was mixed with the solvent to obtain a preliminary slurry solution. This slurry was milled in an Eiger ball mill to achieve the particle size of about 0.8 micron. The solid content in the final milled slurry was determined to be 29.1 wt. %. Coating of this slurry on a flat sheet made of 316 stainless steel, with 0.8 mm thickness (having been acetone-washed and heat-treated at 300° C. previously) resulted in a loading of catalyst of 26.9 wt. %. This loading was determined after air gun treatment to remove excess slurry and following room temperature drying combined with oven drying at 120° C. The final loading after calcining at 450° C. under nitrogen atmosphere was determined to be 25.3 wt. %.

EXAMPLE 2

Coating of ten (10) corrugated sheets that were washed previously with acetone and heat treated at 300° C. with the slurry used in Example 1 was carried out by the following procedures: dip coating, followed by air-knife blowing (at 5 bar), room temperature drying, and oven drying at 120° C. The resultant product showed an average catalyst loading of 25.1 wt. %.

EXAMPLE 3

Coating of a corrugated-type structure packing at 15 mm diameter, height 254 mm, washed with acetone, and heated at 300° C. (for one hour) was carried out using the same slurry described in Example 1. A loading of 23.3 wt. % catalyst was obtained according to the procedures in Example 2.

EXAMPLE 4

A mixed solvent was prepared by mixing 271 grams of distilled water and 54 grams of formamide. A mixture of 147.8 grams of anatase, 27.0 grams of vanadyl oxalate, and 0.20 grams of ammonium phosphate was mixed with the solvent to make a preliminary slurry solution. This slurry then was ball-milled in an Eiger ball mill to achieve a mean particle size of 0.58 microns. The solid content in this slurry was determined to be 29.0 wt. %. Coating of a microfiber mesh structure of 316 stainless steel of 0.8 mm thickness, previously washed with acetone and heat treated in air at 300° C. for 1 hour, in this slurry mixture was determined to have a solid loading of 23.4 wt. % after drying as described in Example 1. Air-knife treatment was used to remove the excess of slurry from support in this case. The particle distribution on the flat sheet appeared to be very even with excellent adhesion, after the drying at 120° C. or after heating at 450° C. in air or nitrogen.

EXAMPLE 5

Coating of two pretreated monoliths as described in Example 1 with the dimension of 15 mm diameter by 25.4 mm height in the slurry, and the drying procedure described in Example 1 gave a catalyst loading of 19.1, and 19.2 wt. %, respectively. An additional thirty (30) monoliths of the same size were prepared subsequently according to this same procedure with virtually identical results.

Examples 1–5 describe the preparation of a catalytic structure to be used in the selective oxidation of o-xylene to phthalic anhydride.

EXAMPLE 6

The support of 5×5 cm is a metal mesh with a thickness of 0.8 mm, stainless steel fibers of 12 μm in diameter and a void volume of 90%. The mesh is immersed in an aqueous solution that contains 10 wt % of Nyacol™ alumina sol. The metal mesh is composed of a plurality of layers of metal fibers. The mesh is connected to the negative pole of a power supply and is placed between and parallel to two vertical metal electrodes, which are connected to the positive pole of a power supply. A potential of 5 V is applied for 60 seconds, during which the sol is coated onto the mesh. The coated product is dried at 150° C. for 20 minutes and subsequently calcined at 500° C. for 1 hour, at which temperature the alumina sol is converted to γ-alumina. The amount of alumina deposited is 21 wt % of the combined alumina and mesh. The coated wire mesh is impregnated at room temperature with 1.10 g of a 3 wt % Ag-containing aqueous solution in which silver oxalate is complexed with ethylene diamine and to which solution cesium hydroxide is added. The impregnated sample is heated in air at 280° C. for 20 minutes. The alumina on the support contains about 10 wt % of Ag and about 150 ppm of cesium.

EXAMPLE 7

The wire mesh is of the same wire dimensions and composition as described in the previous example. The mesh is connected to the power supply and placed in the bath with a 10 wt % slurry of a ground commercially available alumina catalyst support with a surface area of 7.8 $m^2/g$ in water, with 0.18 wt % alumina sol and 0.06 wt % of a commercial quaternary ammonium chloride agent. A potential of 10 V is applied for 2 minutes. The sample is calcined in air at 500° C. for 60 minutes. The amount of catalyst support that is deposited on the mesh is 24.4% by weight of the combined mesh support and catalyst. The coated wire mesh is impregnated at room temperature with 1.0 g of a 7 wt % Ag-containing aqueous solution in which silver oxalate was complexed with ethylene diamine and to which solution cesium hydroxide was added. The impregnated sample is heated in air at 280° C. for 20 minutes. The alumina on the support contains about 20 wt % of Ag and about 150 ppm of cesium.

Examples 6–7 describe the preparation of a catalytic structure to be used in the selective oxidation of ethylene to ethylene oxide.

It is to be understood, however, that the scope of the present invention is not to be limited to the specific embodiments described above. The invention may be practiced other than as particularly described and still be within the scope of the accompanying claims.

What is claimed is:

1. A process for selectively oxidizing an organic molecule, comprising:

selectively oxidizing an organic molecule in a reaction zone by contact with a supported oxidation catalyst on a mesh-like structure, said mesh-like structure comprising a plurality of layers of randomly oriented fibers, said fibers having a diameter of less than 150 microns, said mesh-like structure without the supported catalyst having a void volume of at least 85%, said supported catalyst comprising a selective oxidation catalyst on a particulate support, said particulate support having an average particle size of no greater than 50 microns.

2. The process of claim 1 wherein the mesh-like material comprises at least one of a metal or metal oxide.

3. The process of claim 2 wherein the particulate support has an average particle size of no greater than 20 microns.

4. The process of claim 1 wherein the mesh-like material is in the form of a shaped structured packing.

5. The process of claim 1 wherein the catalyst supported on the particulate support is coated on the mesh-like material.

6. The process of claim 1 wherein the selective oxidation is oxidation of an alkene to an alkylene oxide.

7. The process of claim 1 wherein the selective oxidation is oxidation of o-xylene to phthalic anhydride.

8. The process of claim 1 wherein the selective oxidation is oxidation of propylene to acrolein.

9. The process of claim 1 wherein the selective oxidation is oxidation of propane to acrolein.

10. The process of claim 1 wherein the selective oxidation is oxidation of acrolein to acrylic acid.

11. The process of claim 6 wherein the particulate support has a surface area greater than $25 m^2/g$.

12. The process of claim 1 wherein, in said reaction zone, said mesh-like structure including the supported catalyst has a void volume of at least 60% and no greater than 95%.

13. The process of claim 1 wherein the selective oxidizing is effected in a tubular reactor, and wherein tubes in said tubular reactor include said supported catalyst on said mesh-like structure.

14. A composition comprising:

a selective oxidation catalyst supported on a particulate support that is supported on a mesh-like structure comprising a plurality of layers of randomly oriented fibers, said fibers having a diameter of less than 150 microns, said particulate support having an average particle size no greater than 50 microns, and said mesh-like material without the supported catalyst, has a void volume of at least 85%.

15. The composition of claim 14 wherein the selective oxidation catalyst comprises silver and said catalyst catalyzes the oxidation of ethylene to ethylene oxide.

* * * * *